United States Patent [19]
Zimmon

[11] Patent Number: 5,906,587
[45] Date of Patent: May 25, 1999

[54] APPARATUS AND METHOD FOR THE TREATMENT OF ESOPHAGEAL VARICES AND MUCOSAL NEOPLASMS

[76] Inventor: David S. Zimmon, 7 Farm View Rd., Port Washington, N.Y. 11050

[21] Appl. No.: 08/915,005

[22] Filed: Aug. 20, 1997

Related U.S. Application Data

[62] Division of application No. 08/558,170, Nov. 15, 1995, Pat. No. 5,707,355.

[51] Int. Cl.$^6$ .................................................. A61M 29/00
[52] U.S. Cl. .............................................. 604/49; 604/96
[58] Field of Search ................................ 604/49, 96, 54, 604/27, 28, 101, 104; 606/191, 192, 196

[56] References Cited

U.S. PATENT DOCUMENTS

| | | |
|---|---|---|
| 2,493,326 | 1/1950 | Trinder . |
| 2,499,045 | 2/1950 | Walker et al. . |
| 2,621,651 | 12/1952 | Wallace . |
| 2,849,002 | 8/1958 | Oddo . |
| 3,045,677 | 7/1962 | Wallace . |
| 3,046,988 | 7/1962 | Moreau et al. . |
| 3,154,077 | 10/1964 | Cannon . |
| 3,411,506 | 11/1968 | Valasco . |
| 3,610,247 | 10/1971 | Jackson . |
| 3,734,100 | 5/1973 | Walker et al. . |
| 4,230,108 | 10/1980 | Young . |
| 4,464,175 | 8/1984 | Altman et al. . |
| 4,485,805 | 12/1984 | Foster, Jr. . |
| 4,501,264 | 2/1985 | Rockey . |
| 4,586,505 | 5/1986 | Sisson et al. . |
| 4,710,181 | 12/1987 | Fuqua . |
| 4,729,384 | 3/1988 | Bazenet . |
| 4,832,691 | 5/1989 | Witzel . |
| 5,007,898 | 4/1991 | Rosenbluth et al. . |
| 5,067,497 | 11/1991 | Greear et al. . |
| 5,308,326 | 5/1994 | Zimmon . |
| 5,313,939 | 5/1994 | Gonzalez ............................. 604/54 X |
| 5,330,528 | 7/1994 | Lazim . |
| 5,707,355 | 1/1998 | Zimmon . |

FOREIGN PATENT DOCUMENTS

WO89/00407   1/1989   Australia .

OTHER PUBLICATIONS

S.K. Sarin, M.D. and A. Kumar, M.D., "Sclerosants For Variceal Sclerotherapy: A Critical Appraisal," The American Journal of Gastroenterology; vol. 85, No. 6 1990.

Jeffrey L. Ponsky, MD, John D. Mellinger, MD and Irwin B. Simon, MD, "Endoscopic Retrograde Hemorrhoidal Sclerotherapy Using 23.4% Saline: A Preliminary Report," Gastrointestinal Endoscopy by the American Society for Gastrointestinal Endoscopy, vol. 37, No. 2, 1991.

T. P. Guynn, MD et al., "Injection Sclerotherapy Induced Esophageal Strictures Risk Factors and Prognosis," The American Surgean, vol. 57, Sep. 1991.

(List continued on next page.)

*Primary Examiner*—John D. Yasko
*Attorney, Agent, or Firm*—Woodard, Emhardt, Naughton, Moriarty & McNett

[57] ABSTRACT

A method and apparatus for treating esophageal varices and mucosal neoplasms. In one form of the present invention a balloon tamponade device is utilized to deliver a dressing containing a sclerosant agent to bleeding esophogeal varices. The balloon tamponade delivery results in a uniformed coating of the inflamed site with the treatment agent. The thrombosant agent penetrates the esophageal mucosa, thrombosis esophageal veins and prevents bleeding by provoking an inflammatory response which replaces the squamous esophogeal mucosa with scar tissue to prevent further bleeding from the varices. Another form of the present invention applies therapeutic agents to portions of the esophagus, rectum and/or other mucosal sites such as the urethral bladder, larynx, bronchial tube and vagina. Therapeutic agents containing anti-neoplastic and/or corrosive agents are applied to dressings which are placed in contact with the surface area containing the mucosal neoplasm. After the dressings have been delivered to the surface area they are maintained in contact with the lesion for a period of time. In one form of the present invention the delivery of the therapeutic agents to the lesions is accomplished through a balloon tamponade device.

19 Claims, 4 Drawing Sheets

OTHER PUBLICATIONS

Dennis Miller, MD and K. Beigeleisen, MD, "Sequential Injection of 3% Sodium Tetradecyl Sulfate and 20% Sodium Chloride in the Treatment of Refractory Varicosity of the Greater Saphenous Vein," J Dermatol Surg Oncology, 1994: 20: 329–31.

D. Kahn et al, "A 15 Year Experience of Injection Sclerotherapy in Adult Patients with Extraheptic Portal Venous Obstruction," Annals of Surgery, vol. 219 No. 1, 1994, 34–39.

Jacob Korula et al, "Portal Vein Thrombosis Complicating Endoscopic Variceal Sclerotherapy Convincing Further Evidence, "Digestive Diseases and Sciences vol. 36, No. 8 (Aug. 1991), pp. 1164–1167.

Makoto Hashizume, MD et al., "Endoscopic Ligation of Esophageal Varices Compared with Injection Sclerotherapy: A Prospective Randomized Trial," The American Society for Gastrointestinal Endoscopy, Vo. 39, No. 2, 1993.

Greg V. Stiegmann, M.D., "Endoscopic Management of Esophageal Varices," Advances in Surgery, vol. 27, pp. 207–225, 1994.

Kim L. Isaacs, M.D., Ph.D., "Severe Gastrointestinal Bleeding," Clinics in Geriatric Medicine, vol. 10, No. 1, Feb. 1994.

John S. Goff, MD., "Gastroesophageal Varices: Pathogenesis and Therapy of Acute Bleeding," Gastroenterology Clinics of North America, Vo. 22, No. 4, Dec. 1993.

Neil S. Sadick and Bruce Farber, "A Microbiologic Study of Diluted Sclerotherapy Solutions," J. Dermatol Surg Oncol 1993;19:450–454.

Endoscopic Management of Esophageal Varices, by G.V. Stiegmann, "Advances in Surgery", vol. 27, 1994.-

APPARATUS AND METHOD FOR THE TREATMENT OF ESOPHAGEAL VARICES AND MUCOSAL NEOPLASMS

This application is a division of application Ser. No. 08/558,170, filed Nov. 15, 1995 now U.S. Pat. No. 5,707,355.

BACKGROUND OF THE INVENTION

The present invention relates generally to the treatment of esophageal varices, and more particularly to a method and apparatus for applying sclerosant or thrombosant agents to esophageal varices. Further, the present invention relates to a method for the destruction of mucosal neoplasms by positioning destructive therapeutic agents thereon.

A medical practitioner realizes that it is often necessary to medically treat the variceal veins within the esophagus. Currently, therapeutic techniques such as injection sclerotherapy and band ligation are utilized for the immediate and long term control of hemorrhaging associated with esophageal varices. Injection sclerotherapy involves positioning a long needle within an endoscope and injection various solutions directly into the esophagus. The second therapeutic technique, band ligation utilizes an endoscope to visualize the varix, suck the varix into a banding cap and then release a small rubber band that compresses the site. Both of these therapeutic techniques produce an inflammatory response within the esophageal mucosa that serves to thrombosis the varices and produce long lasting fibrosis in the mucosa that includes the variceal channels and prevents further bleeding.

A limitation common to the prior therapeutic techniques manifests itself in a patient with active bleeding, because active bleeding and associated blood clots cover and obscure the field of view, thereby rendering the procedure difficult to perform. Further, the large dilated esophageal varices fill the esophageal lumen and make it difficult to visualize individual varices or the anatomy, thereby requiring considerable expertise on the part of the practitioner.

Another limitation associated with the prior therapeutic techniques is the general requirement of multiple endoscopic procedures, generally three to six procedures, for the obliteration of varices in the esophagus. Localized trauma, which is a normal part of the prior therapeutic techniques may incite immediate bleeding or produce esophageal ulcers that frequency bleed during the intervals between treatments. Esophageal bleeding may have severe consequences and in certain situations may be life threatening. Further, each endoscopic procedure is expensive, requires that an anesthetic agent be administered to the patient, and is associated with some hazard as well as inconvenience to the patient.

Band ligation and injection sclerotherapy are viewed as being incomplete in the sense that they can not be performed in a uniform manner over the entire mucosa. Consequently, it is possible for a medical practitioner to omit areas and, therefore multiple procedures may be required to ensure that the entire mucosa surface is treated and that all varices are thrombosed and that the mucosa is destroyed. Therefore, the prior techniques may necessitate multiple follow-up examinations and long term surveillance to assure that the mucosa surface has been completely treated.

Although the prior techniques are steps in the right direction for the treatment of esophageal varices, the need for additional improvements still remain. The present invention satisfies this need in a novel and unobvious way.

SUMMARY OF THE INVENTION

A balloon tamponade device for treating esophageal varices, the device comprising: a tube having proximal and distal open ends; a bridle attached to the tube, the bridle being adapted to extend up the esophagus to allow the device to be secured in place while having the proximal open end of the tube positioned within the digestive tract whereby normal feeding and swallowing functions are permitted; a treatment agent; a first inflatable balloon mounted over the tube; the first inflatable balloon having the treatment agent connected thereto; and a first inflation lumen for directing pressurized fluid to inflate the first balloon.

A method of placing a balloon tamponade device for treating esophageal varices comprising: providing a treatment agent; providing a device having a tube having proximal and distal open ends, a first inflatable balloon mounted over the tube, and a first inflation lumen for directing pressurized fluid to inflate the first balloon; backloading the device on an endoscope by passing the endoscope through the open ends of the tube; passing the endoscope through the mouth and down the esophagus and using the endoscope to locate the bleeding site; advancing the device along the endoscope and down the esophagus; applying the treatment agent to the first balloon before advancing the device down the esophagus; and positioning and inflating the first balloon to cause the treatment agent to contact and treat the esophageal varices.

One object of the present invention is to provide an improved device and method for treating esophageal varices.

Another object of the present invention is to provide an improved device and method for treating neoplasms within the digestive tract.

Related objects and advantages of the present invention will be apparent from the following description.

DESCRIPTION OF THE PREFERRED EMBODIMENT

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

As stated above, one preferred embodiment of this invention involves a balloon tamponade device for treating digestive tract bleeding sites. The device includes a tube having proximal and distal open ends, and in inflatable balloon mounted over the tube. An inflation lumen for directing pressurized fluid to inflate the balloon is also provided. A bridle is attached to the tube, and is adapted to extend up the esophagus to allow the device to be secured in place having the proximal open end of the tube positioned within the digestive tract to allow for normal swallowing and feeding functions.

Figure 1:
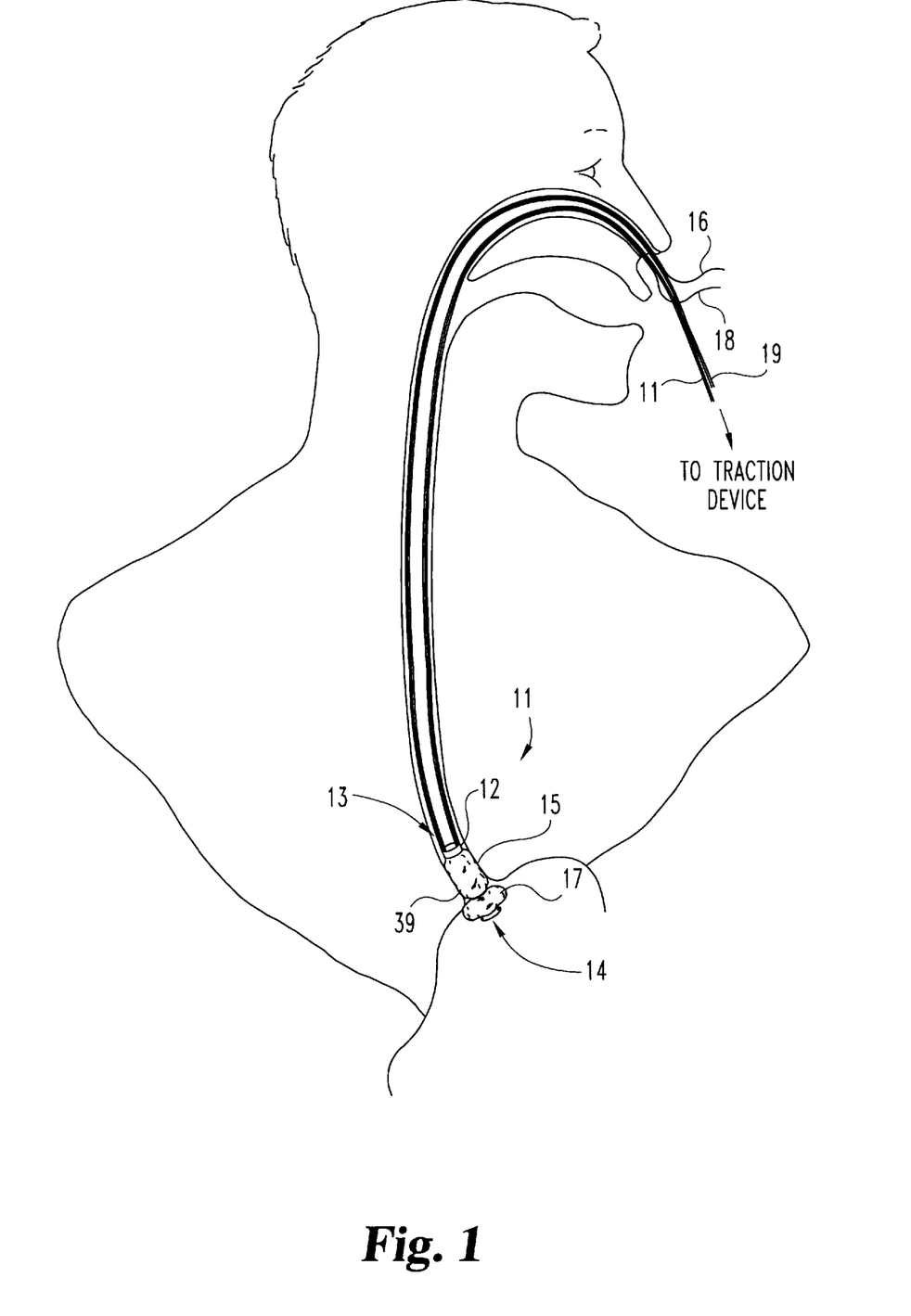
FIG. 1 is a perspective view of a balloon tamponade device according to the present invention in place in a patient.

In one preferred mode, the balloon tamponade device is an esophago-gastric balloon tamponade device for treating esophageal or upper gastric bleeding sites. More specifically, one form of the present invention is utilized to treat esophageal varices. Referring now to FIG. 1, there is shown a perspective view of such a balloon tamponade device 11 according to the present invention in place in a patient. The device 11 includes a tube 12 having a proximal open end 13, and a distal open end 14. An inflatable esophageal balloon 15 is mounted over the tube, and an inflation lumen 16 is provided for directing pressurized fluid to inflate the esophageal balloon 15.

Four wires 19 are attached to the tube 12 and generally form a bridle. The wires 19 extend up the esophagus to allow the device 11 to be secured in place while having the proximal open end 13 of the tube 12 positioned within the esophagus. A gastric balloon 17, is mounted over the tube 12 and is adapted to seat against the gastric cardia when inflated in the stomach and when thereafter the device 11 is pulled with the wires 19 in a direction up the esophagus. A separate inflation lumen 18 is provided to inflate the gastric balloon 17.

Figure 2:
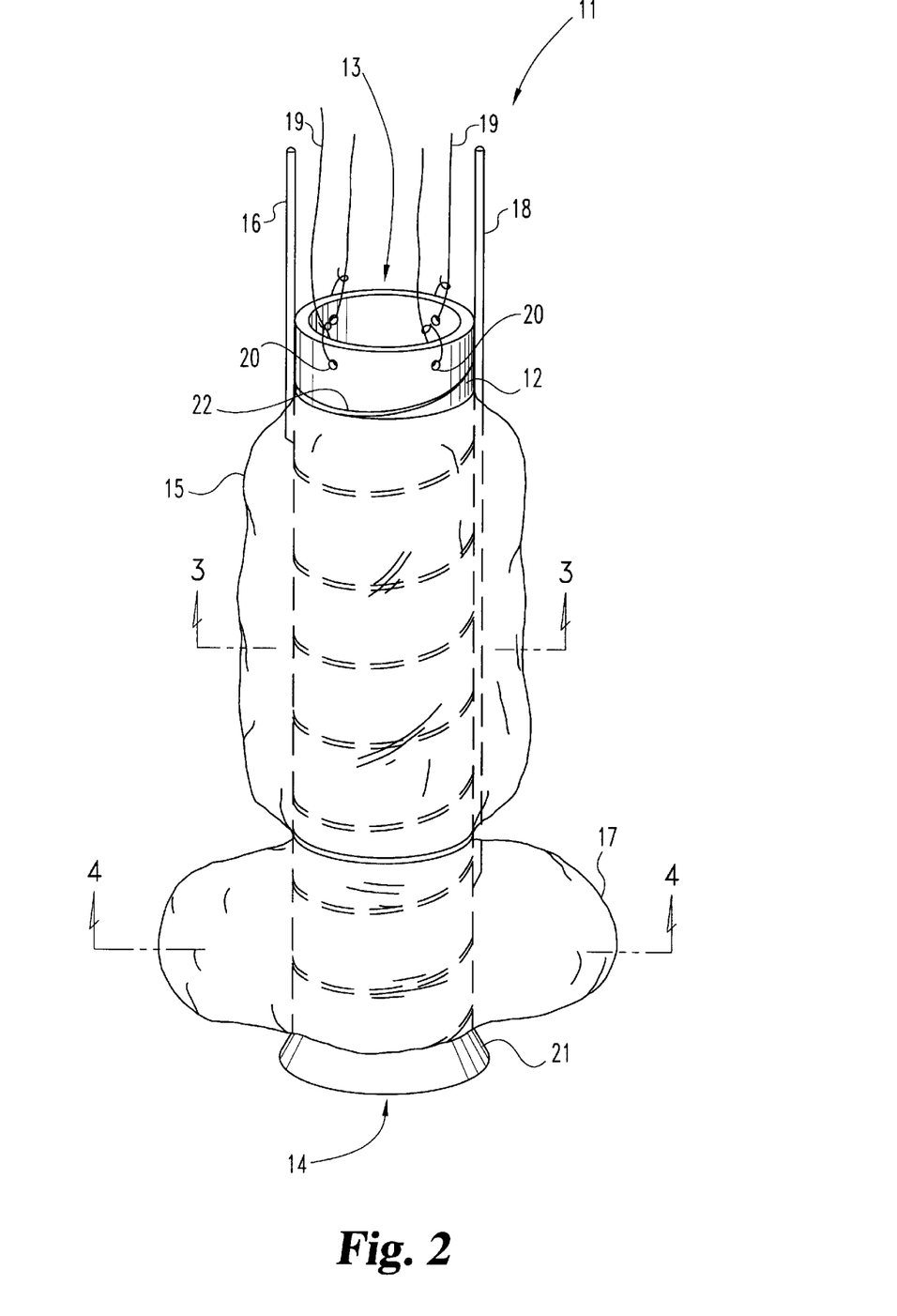
FIG. 2 is an enlarged perspective view of the balloon tamponade device illustrated in FIG. 1. For illustrative purposes, the full lengths of the wires 19 and of the lumens 16 and 18 are not shown.
Figure 3:
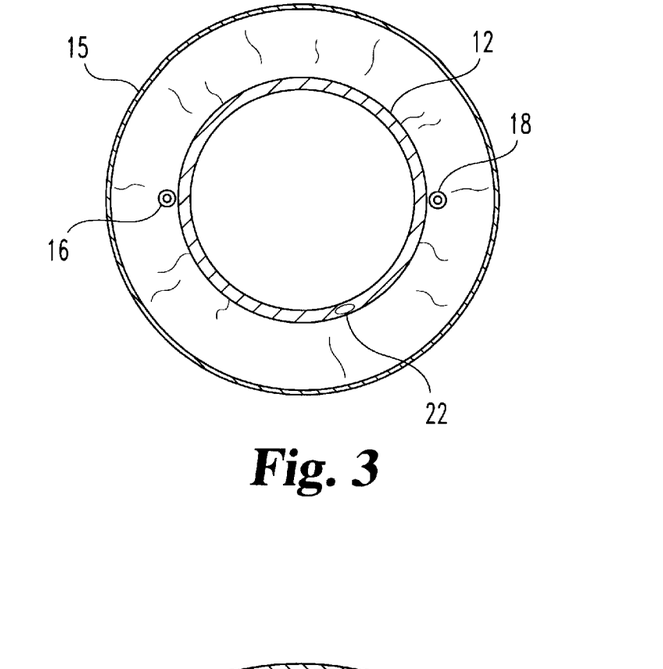
FIG. 3 is a cross-sectional view of the device of FIG. 2 taken along line 3—3 and viewed in the direction of the arrows.
Figure 4:
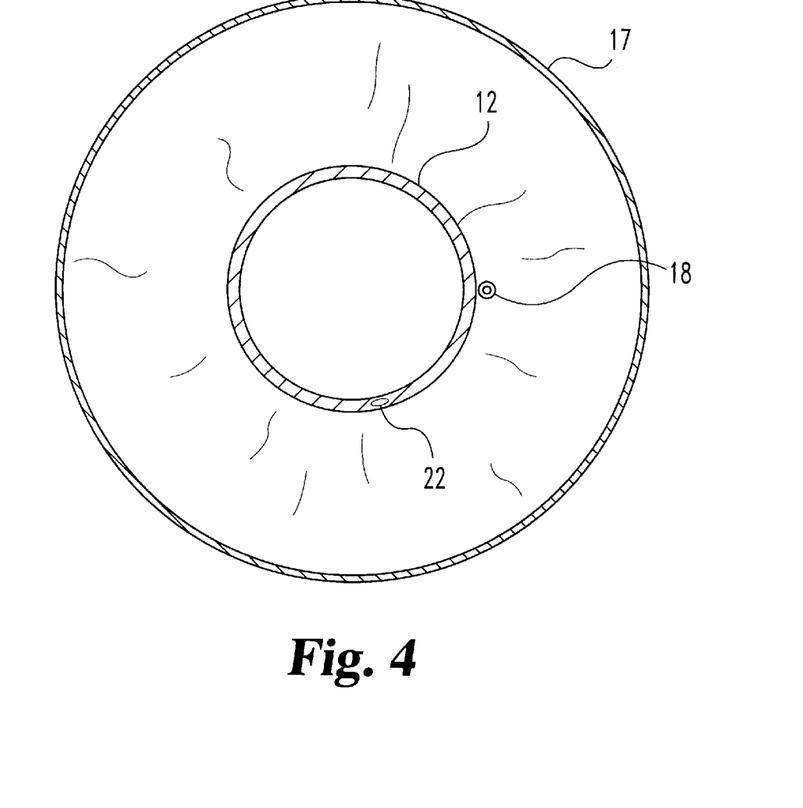
FIG. 4 is a cross-sectional view of the device of FIG. 2 taken along line 4—4 and viewed in the direction of the arrows.

Referring now more particularly to FIGS. 2–4, the tube 12 of the Applicant's preferred device 11 may be made of plastic or another suitable material. The tube 12 is generally of a length so that when the device 11 is in place the tube 12 does not extend upwardly out of the esophagus of the patient. The tube 12 is also sufficiently rigid so that when the esophageal balloon 15 and gastric balloon 17 are inflated, the tube 12 does not collapse, but rather continues to provide a passage through its inner lumen. In Applicant's preferred embodiment, the tube 12 is approximately 8 centimeters in length and is translucent or substantially transparent. Additionally, in a preferred embodiment, the tube 12 contains an embedded wire coil 22 to render the device visible by X-Ray to monitor its position in the patient. The coil 22 may also serve to help prevent the collapse of the tube 12.

It is also preferred that the tube have an inner diameter of about 1.5 cm and an outer diameter of about 2.0 cm. The 1.5 cm diameter is preferred so that even the largest operating upper gastrointestinal endoscopes can be effectively used in connection with the device 11. It is understood, however, that tubes having other dimensions could be used within the scope of the invention herein. Additionally, as illustrated in FIG. 2, the tube 12 may have a flange 21 near its distal open end 14. The flange 21 functions to stabilize the gastric balloon 17.

Turning now to the inflatable esophageal balloon 15 which is mounted over the tube 12, in Applicant's preferred device, the esophageal balloon 15 has a length of about 5 centimeters. In the Applicant's preferred device 11, this facilitates the effective treatment of the distal most 5 cm of the esophagus (the 5 cm of the esophagus closest to the gastro-esophageal junction), which generally contain the most bleeding sites. Also, in the Applicant's preferred device, the esophageal balloon 15 has been of a size such that when inflated, the greatest outer diameter of the device 11 along the inflated esophageal balloon 15 is about 3.0 cm. It is understood, however, that the size of the esophageal balloon 15 can be varied in order to suit a particular patient. As to the means of mounting the balloon over the tube, this may be accomplished by silk ties, bonding or vulcanizing, or any other suitable airtight manner known in the art.

An inflation lumen 16 for directing pressurized fluid to inflate the esophageal balloon 15 is also provided and preferably is bonded to the side of the tube 12. This lumen 16 may be any suitable lumen known in the art for this purpose, and has at least one opening into the esophageal balloon 14 and is of sufficient length to extend up the esophagus and external of the patient when the device is in place.

In Applicant's preferred device 11, a gastric balloon 17 is mounted over the tube 12 near its distal open end 14 to provide means for seating within the stomach. The gastric balloon 17 has an inflated diameter which is sufficiently large so that when positioned in the stomach and then inflated, the gastric balloon 17 seats against and compresses the gastric cardia when the device 11 is pulled with the wires 19 in a direction up the esophagus. In Applicant's preferred device, the gastric balloon 17 is of a size such that when it is inflated, the greatest outer diameter of the device 11 along the gastric balloon 17 is about 10.0 cm. The gastric balloon 17 can be mounted using silk ties, bonding or vulcanizing, or any other suitable airtight method known in the art. An inflation lumen is also provided to direct pressurized fluid to inflate the gastric balloon 17. This lumen could be the same one which inflates the esophageal balloon 15, but in Applicant's preferred devices, a second and separate inflation lumen 18 is provided for the gastric balloon 17, and is also bonded to the side of the tube 12. The inflation lumen 18 passes through the esophageal balloon 15 and into the gastric balloon 17, opening only into the latter. This enables the selective inflation of the esophageal balloon 15 and the gastric balloon 17.

The Applicant's preferred device 11 also includes a plurality of wires 19 which are attached to the tube 12 and generally form a bridle. In Applicant's preferred device 11, the wires 19 are of sufficient length such that when the device 11 is in place, the wires 19 extend up the esophagus and external of the patient (as more clearly illustrated in FIG. 1). Thus the bridal is adapted and operable to allow the device 11 to be secured in place in the patient while having the proximal open end 13 of the tube 12 positioned within the esophagus. This, in turn, provides a convenient passage through which materials can pass to the stomach and enables normal feeding and swallowing functions. The wires 19 are attached to the tube 12 by securing them through small apertures 20 provided near the proximal open end 13 of the tube 12. It is understood, however, that bonding or any other suitable means known in the art could be used to attach the wires 19 to the tube 12. In Applicant's preferred device 11, four wires 19 are provided and attached to the tube 12, but it is understood that three or any other number sufficient to provide stabilization and securing of the device would be adequate. The wires 19 may be constructed of stainless steel or any other suitable material known in the art; however, it is preferred that they may be made of or comprise a suitable radiopaque material, such as platinum, to aid in monitoring the placement of the device 11.

As indicated above, another embodiment of the Applicant's invention relates to a novel method of placing Applicant's devices. In Applicant's preferred method, the placement of the device 11 can be accomplished during upper gastrointestinal endoscopy as a single procedure. Prior to passing an endoscope down the esophagus, the device 11 is backloaded on the endoscope. The endoscope is then passed through the patient's mouth and down the esophagus to determine whether and/or where there are esophageal bleeding sites which need treatment. If treatment is necessary, the endoscope is left positioned down the esophagus, and the device 11 is advanced down over the endoscope using a split overtube or the like until the gastric balloon 17 is positioned within the stomach, leaving at least a portion of the wires 19 remaining external of the patient. Thus, the endoscope acts as an internal guide to assist in properly placing the device 11. In most normal adults, when the overtube has been advanced to a distance of 36 cm, the gastric balloon 17 will be positioned in the stomach. The gastric balloon 17 is then inflated and the bridle wires 19 are pulled until the gastric balloon 18 is felt to seat against the gastric cardia. In some situations, for instance in the case of gastric bleeding sites near the gastro-esophageal junction, effective treatment may be provided simply by having the gastric balloon 17 thus in place. If it is determined that additional treatment is necessary or desirable, the esophageal balloon 15 can then be inflated.

A significant advantage of using an endoscope as a guide means is that the endoscope can be used to monitor position of the device 11 both during and after the placement procedure. Such endoscopic monitoring of position and efficacy at initial placement facilitates immediate adjustment or alternate therapy if necessary. In one of Applicant's favorite methods, after the device 11 is in place, an endoscopic "U" turn is performed in the stomach to view the placement of the device from below. Thereafter, when, as preferred, the tube 12 is translucent or substantially transparent, the endoscope may be withdrawn into the tube 12 and the placement of the device 11 also viewed from within. Additionally, the endoscope can be used to directly observe mucosa both before and during removal of the device 11 to ascertain of bleeding recurs when the balloons are deflated or when the device 11 is repositioned.

As alternative methods of placement, the device 11 may be placed using a balloon introducer such as model number WCPI-1 Prosthesis Introducer manufactured by Wilson-Cook Medical, Inc., of Winston-Salem, N.C., or, during a preceding endoscopy, a wire guide can be passed, and the device 11 can be introduced loaded on a dilator such as a Savary dilator such as model number SGD 14-100 also manufactured by Wilson-Cook Medical, Inc.

Additionally, prior to advancing the device 11 down the esophagus, suitable hemostatic (such as microfibrillar collagen hemostat), coagulant (such as Thrombin, USP), or cytoprotective (such as sucralfate) substances can be applied to the esophageal balloon 14 and/or the gastric balloon 16. Such applications would facilitate effective removal of the device by preventing adherence of the balloons 15 and/or 17 to the bleeding sites.

In another form of the present invention the device 11 is utilized to apply a dressing containing a quantified amount of a sclerosant or thrombosant agent that would penetrate the esophageal mucosa, thrombosis esophageal veins to prevent bleeding and provoke an inflammatory response that would replace the squamous esophageal mucosa with scar tissue to prevent further bleeding from the varices. Prior to advancing device 11 down the esophagus the practitioner applies to the esophageal balloon 14 and/or gastric balloon 17, a quantity of a suitable acidic substance and/or alkaline substance and/or caustic substance. The substance is applied directly to the surface of the balloon and/or is applied to a dressing which is in contact with the balloon. The acidic materials contemplated include tanic acid, picric acid, and salicylic acid that would penetrate the mucosa and produce an intense and inflammatory response of destroyed mucosa and produce thrombosis of adjacent veins. These alkaline substances include sodium hydroxide, sodium carbonate, potassium carbonate, potassium hydroxide or other similar agents. The agents penetrate squamous mucosa with great efficiency and produce an inflammatory response that results in scarring and sclerosis. It is contemplated herein that other materials having similar properties are useable in the current invention. Further, the invention includes the use of caustic substances such as silver nitrate to produce thrombosis of the adjacent veins. Such applications facilitate effective treatment of the esophageal varices to prevent further bleeding from the esophageal varices.

The device 11 and associated methods facilitate uniformly applying the sclerosant and thrombosant agents to produce destructive inflammation and thrombosis of the veins uniformly over the mucosa. The application of the above dressings to the esophageal varices result in the inclusion and thrombosis of the bleeding esophageal varices as well as inciting an inflammatory response to produce long lasting fibrosis and sclerosis of the adjacent veins. Other methods of delivering the sclerosants or thrombosant agents to the surface of the bleeding sites are contemplated by the present invention.

Another form of the present invention is utilized for the destruction of mucosal neoplasms. Neoplasms generally are found in the esophagus, rectum and other mucosal sites such as the urethral bladder, larynx, bronchial tree, and vagina. The application of therapeutic agents to destroy the neoplasms is accomplished through applying dressings containing the anti-neoplastic and/or corrosive agents to the mucosal neoplasms. Suitable dressings are available from E.R. Squibb and Sons Inc., Princeton N.J. The following dressings are available from E.R. Squibb and are known as ZERODERM®, TEGDERM®, DUODERM®, STOMAAHESIVE® and DURA-AHESIVE®.

The device 11 is utilized to deliver and apply the dressings to the surface areas containing the mucosal neoplasms. It is preferred that the dressing uniformly contact the mucosal neoplasm site. After the dressing having the therapeutic agent is delivered to the surface area containing the mucosal neoplasms it is then maintained in contact with the lesion for a specified period of time. The time of contact with the lesion is variable and is best determined by the practitioner based on parameters associated with the lesion. The therapeutic agents being carried by the dressings include anti-neoplastic drugs, such as 5 fluorouracil. Similar therapeutic agents are contemplated as being usable by the present invention. The dressing then must be removable, passed, or dissolved in an appropriate time. Further, a similar method could be applied to treat squamous esophageal, anal or bronchial malignancies or pre-malignant conditions such as Barrett's esophagus with dysplasia or dysplastic lesions in the larynx, bronchi, or rectum.

Still further aspects of the Applicant's preferred method of placing its device 11 relate to the securing of the bridle. Once it has been confirmed that the device 11 is properly in place, a flexible guide tube having first and second open ends is provided. The first end of the guide tube is then placed through the nose and out the mouth of the patient, with the second end of the guide tube remaining external of the nose. Thereafter, the bridle wires 19 and inflation lumens 16 and 18, which are extending out of the mount, are passed into said first end and out said second end of the guide tube. The guide tube is thereafter withdrawn from the nose, thus leaving the bridle wires 19 and lumens 16 and 18 positioned through the patient's nose.

This stage of the procedure is generally shown in FIG. 1. The gastric balloon 17 and esophageal balloon 15 are inflated, and the wires 19 and inflation lumens 16 and 18 are extending out of the nose. The appropriate connectors can then be placed on the inflation lumens 16 and 18 and the bridle wires 19 can be connected to a traction device as necessary. Having the lumens 16 and 18 and the bridle wires 19 thus positioned through the patient's nose increases patient comfort and reduces trauma to the nose and pharynx as compared to nasal passage of larger previously used devices. Additionally, the wires 19 do not interfere with the use of an endoscope to periodically check the positioning of the device 11.

The device 11 can also be used to deliver and apply detachable coatings to treat bleeding sites, such as expandable mesh, foil or gel. As examples, a suitable expandable mesh is available from Sterile Products of Valley Park, Mo., and known as Xeroform. A suitable foil is available from Deseret Medical & Company and known as Oxycel or from United States Surgical Corporation and known as Helistat. A suitable gel is available from Alcon Laboratories and known as Avitene, or from Parke-Davis and known as Thrombin, USP.

To delivery expandable mesh, the mesh can be mounted over the esophageal balloon 15 by laying it on the deflated balloon while softened with a suitable solvent to conform to the shape of the deflated balloon. The mesh material would then expand to its full size on balloon inflation. Alternatively, the mesh material could be applied to the balloon in a cylinder of strips that overlap so that they could expand when the balloon was inflated. The entire mesh assembly could be protected by a gel coating, sleeve, or peel-away wrapper during passage through the mouth and esophagus into position before inflation. Similarly, to deliver foil, the foil can be mounted over the balloon in a fashion identical to the mesh. The gel can be applied to the balloon and dried in place or applied immediately prior to introduction. If necessary, the gel could be protected by a sleeve or peel-away wrapper during introduction.

Thereafter, the device 11 can be advanced to position the esophageal balloon 15 next to the bleeding sites, and the balloon 15 can be inflated. The mesh, foil, or gel would then contact and adhere to the bleeding sites. The balloon 15 of the device 11 can then be deflated, and the device 11 removed, leaving the detachable coating at the bleeding sites.

When being used to deliver detachable coatings, dressings or therapeutic substances, as alternatives to using a balloon in the device 11, other expandable means, for instance, an umbrella-like expandable device activated by hand, spring, screw or hydraulic pressure could also be used as known in the art. Illustrative of this type of device would be the Henning umbrella-type esophageal dilator.

Figure 5:
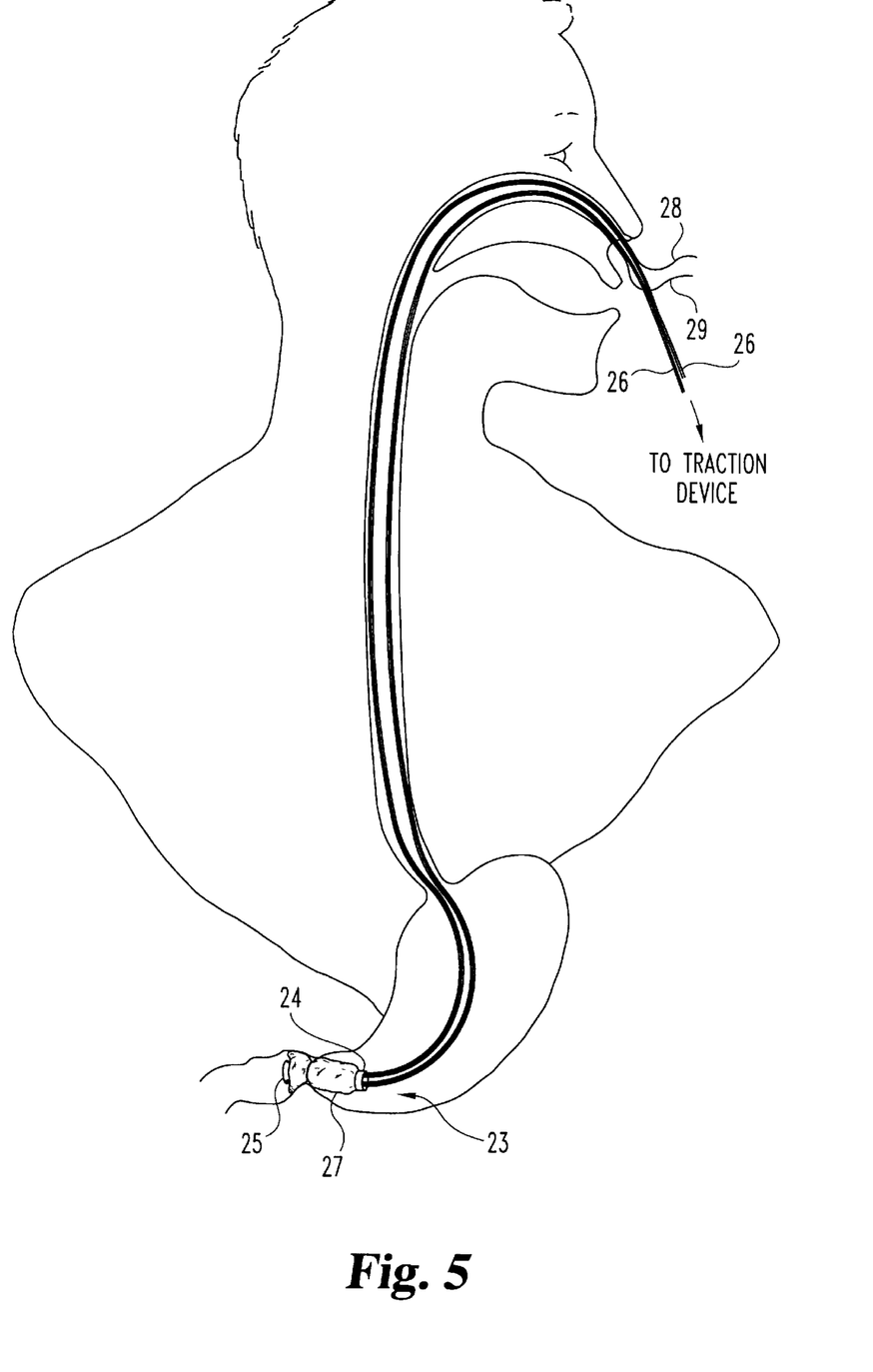
FIG. 5 is a perspective view of a gastroduodenal balloon tamponade device according to the present invention in place in a patient.

As indicated above, in another preferred mode, the Applicant's device for treating digestive track bleeding sites is a gastroduodenal balloon tamponade device for treating duodenal, pyloric or distal gastric bleeding sites. Referring now to FIG. 5, shown in a perspective view of such a gastroduodenal balloon tamponade device 23 in place in a patient. The gastroduodenal balloon tamponade device 23 is similar in construction to the device 11 illustrated in FIGS. 1–4. However, the preferred dimensions of components of the gastroduodenal device 23 are, of course, altered to suit the dimensions of the areas in which the device 23 is normally used (i.e. the lower stomach and duodenum). Accordingly, the device 23 includes a tube 24 which is generally of a length so that when the device 23 is in place the tube 24 extends across the pylorus. In a preferred embodiment, the tube 24 is about 6 centimeters in length but, unlike the preferred device 11 does not include a significant flange near its distal open end. Such a flange might impeded the device's 23 crossing of the pylorus, and thus is not included in the preferred device 23.

The gastroduodenal balloon tamponade device 23 also includes an inflatable duodenal balloon 25 of a size such that when positioned in the duodenum and then inflated, and when the device 23 is then pulled in a direction back toward the stomach by its wires 26, the duodenal balloon 25 seats against and compresses the pylorus and gastric antrum. In the preferred device 23, the duodenal balloon is sized so that when inflated, the greatest outer diameter of the device 23 along the duodenal balloon 25 is about 5 cm. Additionally, the duodenal balloon in the preferred device 23 is about 3 cm in length. These dimensions can, of course, by varied to suit a particular patient.

The gastroduodenal balloon tamponade device 23 also includes an inflatable gastric balloon 27. In Applicant's preferred device 23, the gastric balloon 27 has dimensions such that when the balloon 27 is positioned and inflated in the lower stomach, the balloon 27 compresses distal gastric bleeding sites. The preferred gastric balloon 27 has a length of about 3 cm, and when inflated, the greatest outer diameter of the device 23 along the gastric balloon 27 is about 6 cm. As with the duodenal balloon 25, other gastric balloon 27 sizes can be used to suit particular patients.

The gastroduodenal balloon tamponade device 23 also includes a plurality of wires 26 forming a bridal as well as inflation lumens 28 and 29 for selectively inflating the duodenal balloon 25 and the gastric balloon 27. In the preferred device 23, the wires 26 and the lumens 28 and 29 are sufficiently long to extend through the patient's stomach, up the esophagus and out of the mouth while the device 23 is in place. The bridal is thus adapted to allow the device 23 to be secured in place in the patient while having the proximal open end of the tube 24 position within the stomach. This allows convenient passage of materials from the stomach to the intestine and thus enables normal feeding and swallowing functions.

Additional aspects of the construction of the preferred gastroduodenal balloon tamponade device 23 are analogous to those for the preferred esophago-gastric balloon tamponade device 11 described above.

Another embodiment of the invention as indicated above relates to a method of placing the preferred gastroduodenal balloon tamponade device 23. Generally, this method is analogous to the method described above for placing the preferred esophago-gastric balloon tamponade device 11 with appropriate modification being made, of course, to account for the placement of the device in the duodenum and lower stomach as opposed to the distal esophagus and upper stomach.

Accordingly, the device 23 can be placed during gastrointestinal endoscopy as a single procedure. The device 23 is backloaded onto an endoscope prior to passing the endoscope down the esophagus and through the stomach to determine whether and/or where there are distal gastric, pyloric or duodenal bleeding sites needing treatment. In the event that treatment is needed, the endoscope is positioned in the duodenum and the device 23 is advanced down over the endoscope with a split overtube or using another suitable means for advancing. The advancing is continued until the duodenal balloon 25 is positioned in the duodenum, leaving a portion of the wires 26 and the lumens 28 and 29 of the preferred device 23 external of the patient. Approximately a 70 cm advancement of the device 23 will be sufficient to position the duodenal balloon 25 in the duodenum in most normal adults. This figure will of course vary among patients, and appropriate endoscopic or other known monitoring techniques can be used to assist in the placement of the device 23. Once positioned in the duodenum, the duodenal balloon 25 is then inflated and the bridal wires 26 pulled until the duodenal balloon 25 is felt to seat against the pylorus. Where a patient has bleeding sites in the proximal duodenum, effective treatment can be provided by having just the duodenal balloon 25 thus in place compressing the proximal duodenum. If it is determined that additional treatment in the lower stomach is necessary, the gastric balloon 27 can then be inflated.

In an analogous fashion to the placement of the esophago-gastric tamponade device 11 above, the use of an endoscope as a guide means for placement of the device 23 provides the capability of monitoring the position of the device before and during final placement, as well as upon deflation of the balloons and removal. Additionally, the gastroduodenal tamponade device 23 can also be placed using guide means other than an endoscope, such as a balloon introducer. Also, the bridal wires 26 and lumens 28 and 29 of the gastroduodenal tamponade device 23 can be secured as described for the corresponding components of the device 11 above, and the device 23 can be used to deliver and apply to the lower stomach or duodenum suitable hemostatic or other therapeutic substances such as gels, meshes or foils as described above.

Additional aspects of the use and placement of the duodenal balloon tamponade device 23 are analogous to those described above for the esophago-gastric tamponade device 11.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A method for treating esophageal varices, comprising:
    providing a treatment agent;
    providing a device having an expandable portion;
    placing the treatment agent on the expandable portion;
    positioning the expandable portion adjacent the esophageal varices; and
    expanding the expandable portion to contact the surface of the esophageal varices with the treatment agent to inhibit bleeding from the varices.

2. The method of claim 1, wherein providing a treatment agent includes providing a sclerosant agent.

3. The method of claim 2, which further includes provoking an inflammatory response by applying the treatment agent.

4. The method of claim 3, wherein said expanding the expandable portion further includes uniformly applying the treatment agent to the surface of the esophageal varices.

5. The method of claim 4, wherein there are at least two varices spaced from each other in the esophagus and expanding the expandable portion to contact the surface of each of the esophageal varices is performed to apply a uniform amount of treatment agent to the varices.

6. The method of claim 5, wherein expanding the expandable portion to contact the surface of each of the esophageal varices includes applying pressure to the varices.

7. The method of claim 1, wherein providing a treating agent includes providing a thrombosant agent.

8. The device of claim 1, wherein providing a device includes a device having an expandable portion comprising a first balloon.

9. The method of claim 8, wherein providing a device includes a device having an expandable portion comprising a second balloon.

10. The method of claim 9, wherein the treatment agent is placed only on the first balloon.

11. The method of claim 9, wherein the treatment agent is placed only on the second balloon.

12. The method of claim 1, wherein the treatment agent is placed on the entire expandable portion of the device.

13. A method of treating a plurality of sites within the esophogastric tract, comprising:
    providing a delivery device with an expandable portion and a treatment agent on the expandable portion;
    positioning the expandable portion adjacent the plurality of sites; and
    expanding the expandable portion to deliver the treatment agent to the surface of at least one of the plurality of sites.

14. The method of claim 13, wherein providing a treatment agent includes providing a sclerosant agent.

15. The method of claim 14, further including provoking an inflammatory response by applying the treatment agent.

16. The method of claim 13, wherein providing a treatment agent includes providing a thrombosant agent.

17. The method of claim 13, wherein providing a device includes a device having an expandable portion comprising a first balloon.

18. The method of claim 17, wherein providing a device includes a device having an expandable portion comprising a second balloon.

19. The method of claim 13, wherein the treatment agent is placed on the entire expandable portion of the device.

* * * * *

UNITED STATES PATENT AND TRADEMARK OFFICE
CERTIFICATE OF CORRECTION

PATENT NO : 5,906,587
DATED : May 25, 1999
INVENTOR(S) : David S. Zimmon It is certified that error appears in the above-identified patent and that said Letters Patent are hereby corrected as shown below:

In column 3, line 2, please change the word "in" to --an--.
In column 5, line 51, please change "gastric balloon 16" to --gastric balloon 17--.
In column 10, line 46, claim 17, please change "method" to --device--.

Signed and Sealed this

Twenty-ninth Day of May, 2001

Attest:

NICHOLAS P. GODICI

Attesting Officer

Acting Director of the United States Patent and Trademark Office